US007189418B2

(12) United States Patent
Hiratsuka et al.

(10) Patent No.: US 7,189,418 B2
(45) Date of Patent: Mar. 13, 2007

(54) METHOD FOR EXTRACTING LIPID MIXTURE CONTAINING PHOSPHOLIPIDS COMPRISING POLYUNSATURATED FATTY ACIDS FROM VISCERA OF FISH, METHOD FOR PRESERVING VISCERA PRIOR TO EXTRACTION, AND LIPID MIXTURE EXTRACTED THEREBY

(75) Inventors: Seiichi Hiratsuka, Shizuoka (JP); Toshihiro Suzuki, Shizuoka (JP); Masayuki Hashidume, Yaizu (JP); Youko Matsue, Yaizu (JP); Tomoko Kitagawa, Yaizu (JP); Masaaki Yokoyama, Yaizu (JP); Masami Tamura, Yaizu (JP); Tatsuya Fujii, Yaizu (JP); Noriyuki Muramatsu, Yaizu (JP)

(73) Assignees: Kabushikikaisha Maruhachi Muramatsu, Shizuoka (JP); Shizuoka Prefectural Government, Shizuoka (JP)

( * ) Notice: Subject to any disclaimer, the term of this patent is extended or adjusted under 35 U.S.C. 154(b) by 612 days.

(21) Appl. No.: 10/365,050

(22) Filed: Feb. 12, 2003

(65) Prior Publication Data
US 2003/0190392 A1 Oct. 9, 2003

(30) Foreign Application Priority Data
Mar. 29, 2002 (JP) ............................. 2002-095004
Mar. 29, 2002 (JP) ............................. 2002-095183
Jan. 6, 2003 (JP) ............................. 2003-000645

(51) Int. Cl.
*A61K 45/00* (2006.01)
*A61K 47/44* (2006.01)
*A61K 35/60* (2006.01)

(52) U.S. Cl. .................. 424/523; 424/283.1; 424/520; 424/522

(58) Field of Classification Search ................ 424/523, 424/520, 522, 283.1
See application file for complete search history.

(56) References Cited
U.S. PATENT DOCUMENTS 2,171,594 A * 9/1939 Nitardy ....................... 424/553
2,406,249 A * 8/1946 Parfentjev ................... 424/551
5,484,611 A     1/1996 Noble et al. ................ 424/570
5,965,413 A * 10/1999 Sakai et al. ................. 435/106
6,955,831 B2 * 10/2005 Higgs et al. ................ 426/630

FOREIGN PATENT DOCUMENTS

| CA | 867 691 | 4/1971 |
| CN | 1114869 | 1/1996 |
| JP | 06-77505 B2 | 10/1994 |
| JP | 08-198754 | 8/1996 |
| JP | 08-325192 | 12/1996 |
| JP | 08-325192 A | 12/1996 |
| JP | 10-017475 | 1/1998 |
| WO | 90/08179 | * 7/1990 |

OTHER PUBLICATIONS

Bosund et al., "Effect of pre-cooking of Baltic herring on lipid hydrolysis during subsequent cold storage", *Levensmittel Wissenchaft und Technologie*, vol. 2, No. 3, 1969 pp. 59-61.
Cho et al., "Oxidative stability of lipids from squid tissues", *Fisheries Science*, vol. 67, No. 4, 2001, pp. 738-743.
Biosis Online, AN=PREV199598234113, Takiguchi Akihide, "Differences between deterioration of the lipids in roasted and unroasted seasoned-dried filefish products during storage", *Nippon Suisan Gakkaishi*, vol. 61, No. 1, 1995 pp. 51-57.
English Translation of Office Action Issued Dec. 1, 2005 in Corresponding Chinese Patent Application No. 03807522.9.

* cited by examiner

*Primary Examiner*—Ruth A Davis
(74) *Attorney, Agent, or Firm*—Knoble Yoshida & Dunleavy, LLC

(57) ABSTRACT

The present invention provides a method for extracting a lipid mixture having a high percentage of phospholipids comprising polyunsaturated fatty acids. The method comprises the steps of (a) heating the viscera of fish with hot water or steam; and (b) extracting from the heated viscera of fish, using a solvent, the lipid mixture containing phospholipids comprising polyunsaturated fatty acids. The lipid mixture obtained by the present method contains phosphatidylserine comprising docosahexaenoic acid and phosphatidylethanolamine comprising docosahexaenoic acid in high concentration.

10 Claims, No Drawings

US 7,189,418 B2

METHOD FOR EXTRACTING LIPID MIXTURE CONTAINING PHOSPHOLIPIDS COMPRISING POLYUNSATURATED FATTY ACIDS FROM VISCERA OF FISH, METHOD FOR PRESERVING VISCERA PRIOR TO EXTRACTION, AND LIPID MIXTURE EXTRACTED THEREBY

CROSS-REFERENCE TO RELATED APPLICATIONS

This application claims the benefit of Japanese Patent Application No. 2002-95183 filed on Mar. 29, 2002, Japanese Patent Application No. 2002-95004 filed on Mar. 29, 2002, and Japanese Patent Application No. 2003-00645 filed Jan. 6, 2003, the entire contents of which are incorporated by reference.

FIELD OF THE INVENTION

The present invention relates to a method for extracting, from the viscera of fish that are obtained as a byproduct in the seafood processing industry, a lipid mixture containing phospholipids comprising polyunsaturated fatty acids, and also to a method for preserving the viscera for a certain time period prior to the extraction.

BACKGROUND OF THE INVENTION

In recent years, it has been disclosed that phospholipids, comprising polyunsaturated fatty acids such as eicosapentaenoic acid or docosahexaenoic acid (DHA), play an important role in physiology. The viscera of tuna, bonito, sardine and other fish contain an abundance of these phospholipids, and have drawn much attention as a candidate material for functional food. The viscera of fish are a byproduct rather than a main product in the seafood processing industry, and thus most are discarded. Therefore, an effective use of these viscera is beneficial from the viewpoint of waste reduction as well as of maximum resource utilization.

Since a polyunsaturated fatty acid such as eicosapentaenoic acid or docosahexaenoic acid is present in the viscera of fish as a constituent of phospholipid, it is important to develop a technique to efficiently extract highly concentrated phospholipids from the viscera of fish.

A type of phospholipid called phosphatidylserine is found to be effective in improving dementia, depression, and brain functions such as memory, as well as in strengthening an athlete's muscles. Thus its application to food and medicine is highly anticipated. Phosphatidylserine comprising docosahexaenoic acid is present in a human retina or brain. Phosphatidylethanolamine, which is also a type of phospholipid, is found to have an antioxidation effect, among others. Phosphatidylethanolamine comprising docosahexaenoic acid is also present in a human retina or brain. A special attention has been paid to phosphatidylserine comprising docosahexaenoic acid and phosphatidylethanolamine comprising docosahexaenoic acid, since the decrease in docosahexaenoic acid in the brain due to aging occurs in proportion to the decrease in phosphatidylserine and phosphatidylethanolamine.

However, the viscera of fish contain phospholipase, which is an enzyme that decomposes phospholipids. Therefore, the phospholipids in an organism are decomposed by phospholipase over time, leading to a gradual decrease in the amount of extractable phospholipids. Thus, it is desirable that phospholipids be extracted while the viscera are still fresh, preferably immediately after the viscera are collected from a store or a processing factory.

However, in reality, it is very difficult to set up a work schedule to extract phospholipids from viscera at a factory or the like immediately after collection. Usually, the collected viscera are temporarily frozen or freeze-dried to stop the activity of phospholipase, and are thawed later for processing.

Techniques to extract phospholipids from once freeze-dried viscera of fish are disclosed in Publicly Announced Patent Journal No. HEI 6 [1994]-77505 and Laid-Open Patent Journal No. HEI 8 [1996]-325192.

There is a problem, however, in the freezing or freeze-drying methods for preserving viscera. That is, the freezing or freeze-drying methods only suspend the activity of phospholipase (catabolic enzyme) present in the raw material; they do not completely eliminate the activity. Therefore, it is construed that decomposition of phospholipids progresses during the freezing process until the viscera are completely frozen. Also, during the thawing process, phospholipase is reactivated, decomposing phospholipids in the viscera over time, leading to an increase in neutrolipids and a decrease in phospholipids. Therefore, to obtain phospholipids in high concentration, quick-freezing and quick-thawing processes are needed. These techniques require high cost, a huge equipment installation area, and extensive maintenance.

BRIEF SUMMARY OF THE INVENTION

Accordingly, it is an object of this invention to provide a simple and low-cost method for obtaining phospholipids in high concentration by deactivating the catabolic enzyme of phospholipids contained in live fish, and to provide phospholipids manufactured by this method.

It is another object of the present invention to provide a method for preserving the viscera of fish without reducing the phospholipid content for later extraction.

It is a further object of the present invention to obtain from the viscera of fish phosphatidylserine comprising docosahexaenoic acid and phosphatidylethanolamine comprising docosahexaenoic acid in high concentration.

Through a series of studies to find the best method for preserving the viscera of fish for a long time without allowing decomposition of phospholipids in the viscera to progress, the inventors found that promptly boiling or steaming the collected viscera at a predetermined temperature can achieve the objective.

That is, when the viscera of fish are preserved for the purpose of phospholipids extraction, pre-boiling the viscera deactivates the catabolic enzyme of phospholipids, thereby minimizing the loss of phospholipids during preservation. A lipid mixture containing phospholipids is extracted from the boiled viscera by use of a solvent, and the extracted lipid mixture is separated into individual lipids by a method such as chromatography. The process results in phospholipids comprising useful polyunsaturated fatty acids in high concentration.

Furthermore, during the course of the present study, the inventors unexpectedly found that the extract has a phospholipid content that is higher when the viscera of fish are processed after being boiled, than when the viscera are processed raw.

According to the first aspect of this invention, there is provided a method for extracting a lipid mixture from the viscera of fish, wherein the extraction method comprises the steps of (a) heating the viscera of fish; and (b) extracting the lipid mixture containing phospholipids comprising polyunsaturated fatty acids from the heated viscera of fish using a solvent. This method further comprises a step of (c) preserving the heated viscera in refrigeration or frozen until the step of extracting the lipid mixture is applied.

According to the second aspect of this invention, there is provided a method for preserving the viscera of fish for a predetermined time, before extracting the lipid mixture containing phospholipids comprising polyunsaturated fatty acids from the viscera of fish using a solvent, wherein the viscera-preserving method comprises the steps of (a) heating the viscera of fish; and (b) preserving the heated viscera in refrigeration or frozen.

According to the third aspect of this invention, there is provided a lipid mixture obtained by a method comprising the steps of (a) heating the viscera of fish; and (b) extracting the lipid mixture containing phospholipids comprising polyunsaturated fatty acids from the heated viscera of fish using a solvent. The lipid mixture preferably contains phosphatidylserine comprising docosahexaenoic acid and phosphatidylethanolamine comprising docosahexaenoic acid.

According to the fourth aspect of this invention, there is provided phosphatidylserine, wherein the proportion of phosphatidylserine comprising docosahexacnoic acid is 45% or higher by weight of the total phosphatidylserine.

According to the fifth aspect of this invention, there is provided phosphatidylethanolamine, wherein the proportion of phosphatidylethanolamine comprising docosahexaenoic acid is 35% or higher by weight of the total phosphatidylethanolamine.

DETAILED DESCRIPTION OF THE PREFERRED EMBODIMENTS

Through a series of studies to find the best method for preserving the viscera of fish for a long time without allowing decomposition of phospholipids in the viscera to progress, the inventors found that promptly boiling or steaming the collected viscera at a predetermined temperature can achieve the objective.

The following three methods can be utilized for deactivating enzymes: adding a chelating agent, varying pH, and heating.

The method of adding a chelating agent is often used for deactivating enzymes in a liquid-state material, since it can be easily dissolved in liquids. However, to deactivate enzymes in a solid-state material as in the present case, this method is not suitable. This is because it takes a long time for a chelating agent to penetrate through the material, requiring, for example, 24-hour immersion of the material in a chelating agent. Furthermore, deactivation does not always complete even after such a long time.

The method of varying pH may damage the raw material itself, possibly decomposing DHA-bonded phospholipids. In addition, salt is formed when pH is neutral, requiring a desalting process which poses a cost disadvantage due to equipment investment on a desalting machine or the like.

In the heating method, on the other hand, the raw material can be heated, for example, in a water bath allowing heat transfer through the center, ensuring deactivation of phospholipase. By use of this method it is also possible to remove water-soluble impurities such as various extract components of the raw material. Therefore, this heating method offers an economical way of obtaining DHA-bonded phospholipids in high concentration, without invoking high equipment cost.

In the method of heating the raw material in a water bath, the higher the temperature is and the longer the heating time is, the more thoroughly done the deactivation of the enzyme is. However, processing the raw material at unnecessarily high temperatures for an unnecessarily long time will cause decomposition of DHA-bonded phospholipids, thereby rendering it difficult to obtain DHA-bonded phospholipids in high concentration. Generally, enzymes are deactivated at a temperature of 60° C. or higher. From the health standpoint, food should not contain coli bacilli. Thus, the material should be processed at a high enough temperature to kill coli bacilli, i.e. 60° C. or higher; preferably it should be processed at a temperature between 80° C. and 110° C. Therefore, it is preferable to set the lowest temperature limit at 60° C. for the process of deactivating catabolic enzymes of phospholipids.

Processing the material at a temperature of 60° C. or higher elutes neutrolipids and water-soluble components (organic acids, amino acids, amines, etc.), and also decreases a moisture content, thereby making it possible to extract a lipid mixture with fewer impurities and less fishy smell. If fishy smell is still a concern, a deodorizing process such as treating the material with activated charcoals or aluminum silicate may also be applied after the solvent extraction.

Boiling is not the only method for heating the material. What is required is the placement of the material in an environment with a temperature of 60° C. or higher. The material may be immersed in hot water, or may be heated by injecting or spraying hot water or steam onto the material.

The heating time is preferably within 180 minutes as demonstrated in the embodiments described later. Heating for 10 minutes to 90 minutes is most preferable.

The material used in the present invention includes red-flesh fish such as bonito, tuna, mackerel, and sardine, or white-flesh fish such as cod, sea bream, flounder, flatfish, and shark, and salmon and trout. The viscera used in the present invention include ovary, testis, heart, liver, stomach, intestines, etc. In particular, the testis of bonito or tuna is most suitable in terms of the extraction yield of phospholipids. The use of testis, which is a byproduct in the seafood processing industry, is preferable also from the cost aspect.

The phospoholipids extracted by the present invention include phosphatidylserine comprising docosahexaenoic acid and phosphatidylethanolamine comprising docosahexaenoic acid. These phospoholipids have recently been found to have useful physiological effects.

For extraction after boiling, an organic solvent or a mixed solvent of an organic solvent and water may be used. Examples of organic solvents are ethanol, methanol, propanol, ethylether, hexane, and chloroform.

Separation of phosphatidylserine or phophatidylethanolamine from the lipid mixture can be performed by chromatography, for example. According to the present invention, separation of the lipid mixture results in phosphatidylserine wherein the proportion of phosphatidylserine comprising docosahexaenoic acid is 45% by weight or higher of the total phosphatidylserine; and phosphatidylethanolamine wherein the proportion of phosphatidylethanolamine comprising docosahexaenoic acid is 35% by weight or higher of the total phosphatidylethanolamine. Therefore, the lipid mixture according to the present invention has a docosahexaenoic acid content that is higher than ever observed, showing usefulness as a material for food and medicine.

Phosphatidylserine wherein the proportion of phosphatidylserine comprising docosahexaenoic acid is 45% by weight or higher and phosphatidylethanolamine wherein the proportion of phosphatidylethanolamine comprising docosahexaenoic acid is 35% by weight or higher are similar to biological components. Thus their application to medicine, among others, is particularly anticipated.

Phospholipids other than phosphatidylserine and phosphatidylethanolamine in the lipid mixture are phosphatidyl choline, lysophosphatidyl choline, and lysophosphatidylethanolamine, for example. Constitutive fatty acids in phospholipids other than docosahexaenoic acid are palmitic acid, oleic acid, eicosapentaenoic acid, and docosapentaenoic acid, for example.

Having described the invention, the following embodiments are given to illustrate specific applications of the invention including the best mode now known to perform the invention. These specific embodiments are not intended to limit the scope of the invention described in this application.

Embodiment 1:

At a dried bonito factory in the city of Yaizu in the prefecture of Shizuoka, the ovary (Table 1) and the testis (Table 2) obtained as byproducts when the bonitos are fresh cut were respectively boiled, promptly after collection, over time in hot water at 95° C.

After measuring the moisture content, the lipid mixture was extracted by a method that is a variation of the Bligh and Dyer method. After removing the solvent, an organoleptic test based on odor was administered. After elution with a solvent again, the lipid mixture was separated into neutrolipids and phospholipids by using silica cartridges. After removing the solvent, the mixture ratio of lipids was evaluated.

Also, to confirm the effect of the hot water process according to the present invention, the control segments were selected to be those that were promptly analyzed raw immediately after collection (Control 1), and those that were analyzed after refrigeration for two days without hot water processing immediately after collection (Control 2), and were compared with the hot water processed segments according to the present embodiment. The hot water processed segments were analyzed after refrigeration for two days after hot water processing.

TABLE 1

Bonito Ovary Hot Water Processing Test (Bonito Ovary 95° C. Boiling Test)

| Test Segment | NL (%) | PL (%) | MO (%) | Percentage of decrease in weight of ovary |
|---|---|---|---|---|
| Control 1 (Immediately after collection) | 65.2 | 34.8 | 70.5 | 0.0 |
| Control 2 (2 days of refrigeration) | 74.0 | 26.0 | 70.9 | 2.1 |
| 2 days of refrigeration after boiling for 10 minutes | 55.4 | 44.6 | 63.4 | 17.4 |
| 2 days of refrigeration after boiling for 30 minutes | 47.2 | 52.8 | 58.6 | 33.2 |
| 2 days of refrigeration after boiling for 60 minutes | 51.7 | 48.3 | 57.8 | 33.8 |
| 2 days of refrigeration after boiling for 90 minutes | 51.6 | 48.4 | 57.0 | 33.9 |

*NL stands for neutrolipid; PL stands for phospholipid; and MO stands for moisture content.

TABLE 2

Bonito Testis Hot Water Processing Test (Bonito Testis 95° C. Boiling Test)

| Test Segment | NL (%) | PL (%) | MO (%) | Percentage of decrease in weight of testis |
|---|---|---|---|---|
| Control 1 (Immediately after collection) | 29.2 | 70.8 | 80.7 | 0.0 |
| Control 2 (2 days of refrigeration) | 42.2 | 57.8 | 80.5 | 1.9 |
| 2 days of refrigeration after boiling for 10 minutes | 25.1 | 74.9 | 79.6 | 7.6 |
| 2 days of refrigeration after boiling for 30 minutes | 26.7 | 73.3 | 78.3 | 10.7 |
| 2 days of refrigeration after boiling for 60 minutes | 26.0 | 74.0 | 78.0 | 11.8 |
| 2 days of refrigeration after boiling for 90 minutes | 25.9 | 74.1 | 77.8 | 13.8 |

*NL stands for neutrolipid; PL stands for phospholipid; and MO stands for moisture content.

We can see from Tables 1 and 2 that, in Control 2 where no boiling was applied, the phospholipid content decreased significantly due to the two days of refrigeration for both the ovary and the testis. This is due to the fact that phospholipase (catabolic enzyme of phospholipids) was activated, decomposing the phospholipids during refrigeration. Also in Control 2, we can see that the neutrolipid content increased while the phospholipid content decreased.

On the other hand, in the hot water processed segments according to the present embodiment, no decrease in the phospholipid content was observed even after preservation for two days. This is due to the fact that the boiling process deactivated phospholipase. Furthermore, as compared to Control 2, in all of the hot water processed segments for 10 minutes to 90 minutes, not only the decrease in the phospholipid content was suppressed by the deactivation of the catabolic enzyme of phospholipids, but also the phospholipid content itself increased.

Furthermore, as is clear in comparison with Control 1 wherein analyses were performed immediately after collection, the phospholipid content is higher in the hot water processed segments than in the raw stage.

In addition, it was found in the hot water processed segments that the moisture content decreased in both cases of the ovary and testis, and that the weight of each organ decreased more than the weight of moisture.

Furthermore, the organoleptic test showed that the hot water processed segments clearly had less fishy odor than Control 1 (extracted immediately after collection) and Control 2 (extracted after two days of refrigeration).

Tables 3 through 6 show the results for the cases wherein the hot water processing temperatures were 70° C. and 85° C., with the processing and analyses performed in the same manner as mentioned above.

TABLE 3

Bonito Testis Hot Water Processing Test (Bonito Testis 70° C. Boiling Test)

| Test Segment | NL (%) | PL (%) | MO (%) | Percentage of decrease in weight of testis |
|---|---|---|---|---|
| Control 1 (Immediately after collection) | 29.2 | 70.8 | 80.7 | 0.0 |

TABLE 3-continued

Bonito Testis Hot Water Processing Test (Bonito Testis 70° C. Boiling Test)

| Test Segment | NL (%) | PL (%) | MO (%) | Percentage of decrease in weight of testis |
|---|---|---|---|---|
| Control 2 (2 days of refrigeration) | 42.2 | 57.8 | 79.6 | 1.9 |
| 2 days of refrigeration after boiling for 10 minutes | 29.1 | 70.9 | 79.8 | 5.8 |
| 2 days of refrigeration after boiling for 30 minutes | 30.8 | 69.2 | 80.5 | 5.9 |
| 2 days of refrigeration after boiling for 60 minutes | 27.6 | 72.4 | 80.4 | 6.1 |
| 2 days of refrigeration after boiling for 90 minutes | 27.7 | 72.3 | 80.1 | 6.0 |

*NL stands for neutrolipid; PL stands for phospholipid; and MO stands for moisture content.

TABLE 4

Bonito Testis Hot Water Processing Test (Bonito Testis 85° C. Boiling Test)

| Test Segment | NL (%) | PL (%) | MO (%) | Percentage of decrease in weight of testis |
|---|---|---|---|---|
| Control 1 (Immediately after collection) | 29.2 | 70.8 | 80.7 | 0.0 |
| Control 2 (2 days of refrigeration) | 42.2 | 57.8 | 80.5 | 1.9 |
| 2 days of refrigeration after boiling for 10 minutes | 26.2 | 73.8 | 80.2 | 7.1 |
| 2 days of refrigeration after boiling for 30 minutes | 27.0 | 73.0 | 79.6 | 10.0 |
| 2 days of refrigeration after boiling for 60 minutes | 27.0 | 73.0 | 78.5 | 10.9 |
| 2 days of refrigeration after boiling for 90 minutes | 27.2 | 72.8 | 78.0 | 11.4 |

*NL stands for neutrolipid; PL stands for phospholipid; and MO stands for moisture content.

TABLE 5

Bonito Ovary Hot Water Processing Test (Bonito Ovary 70° C. Boiling Test)

| Test Segment | NL (%) | PL (%) | MO (%) | Percentage of decrease in weight of ovary |
|---|---|---|---|---|
| Control 1 (Immediately after collection) | 65.2 | 34.8 | 70.5 | 0.0 |
| Control 2 (2 days of refrigeration) | 74.0 | 26.0 | 70.9 | 2.1 |
| 2 days of refrigeration after boiling for 10 minutes | 66.8 | 33.2 | 71.3 | 9.9 |
| 2 days of refrigeration after boiling for 30 minutes | 66.4 | 33.6 | 66.0 | 22.5 |
| 2 days of refrigeration after boiling for 60 minutes | 63.7 | 36.3 | 64.7 | 23.0 |
| 2 days of refrigeration after boiling for 90 minutes | 64.3 | 35.7 | 64.9 | 23.7 |

*NL stands for neutrolipid; PL stands for phospholipid; and MO stands for moisture content.

TABLE 6

Bonito Ovary Hot Water Processing Test (Bonito Ovary 85° C. Boiling Test)

| Test Segment | NL (%) | PL (%) | MO (%) | Percentage of decrease in weight of ovary |
|---|---|---|---|---|
| Control 1 (Immediately after collection) | 65.2 | 34.8 | 70.5 | 0.0 |
| Control 2 (2 days of refrigeration) | 74.0 | 26.0 | 70.9 | 2.1 |
| 2 days of refrigeration after boiling for 10 minutes | 57.5 | 42.5 | 64.0 | 15.4 |
| 2 days of refrigeration after boiling for 30 minutes | 55.5 | 44.5 | 49.0 | 30.0 |
| 2 days of refrigeration after boiling for 60 minutes | 49.8 | 50.2 | 58.5 | 32.1 |
| 2 days of refrigeration after boiling for 90 minutes | 48.8 | 51.2 | 58.0 | 33.2 |

*NL stands for neutrolipid; PL stands for phospholipid; and MO stands for moisture content.

In Tables 3 through 6 again, as compared to Control 2, in all of the hot water processed segments for 10 minutes to 90 minutes, not only the decrease in the phospholipid content was suppressed by the deactivation of the catabolic enzyme of phospholipids, but also the phospholipid content itself increased.

We can see that phospholipase (catabolic enzyme of phospholipids) is deactivated at 70° C. after 10 minutes. Also, as the moisture content decreased, and water and water-soluble elements (organic acid, amino acid, and amines) were removed by boiling, the fishy odor decreased.

In the present embodiment, the viscera of fish were processed in hot water at 60° C. or higher, and then extraction with a solvent was performed without changing the state of the viscera. However, this is not the only method according to the present invention. For example, the viscera of fish may be dried after processing in hot water of 60° C. or higher, and after the drying, extraction with a solvent may be performed.

Embodiment 2

At a dried bonito factory in the city of Yaizu in the prefecture of Shizuoka, the testis of bonito obtained as a byproduct was boiled at 60° C.~100° C. After extraction with ethanol, the ethanol was removed and a lipid mixture was obtained.

The lipid mixture according to the present embodiment obtained in this manner contained neutrolipids 27.6% by weight and phospholipids 72.4% by weight. For a comparative example, the lipid mixture obtained by extraction with ethanol immediately after collecting the testis of bonito contained neutrolipids 30.7% by weight and phospholipids 69.3% by weight. Therefore, a lipid mixture with a high phospholipid content was obtained according to the present embodiment.

High Performance Liquid Chromatography (HPLC) was employed to separate phosphatidylserine from the phospholipids in the lipid mixture obtained according to the present embodiment. The phosphatidylserine content was very high: 9.5% by weight~12.7% by weight [12.7 wt. % (Sample 1), 12.4 wt. % (Sample 2), 9.6 wt. % (Sample 3), 9.5 wt. % (Sample 4) (average of Sample 1~Sample 4=11.05 wt. %)] of the total amount of phospholipids. Also, analyses per Gas Chromatography (GC) were performed on the fatty acids in the phosphatidylserine. It was found that the proportion of phosphatidylserine comprising docosahexaenoic acid was very high: 50.2% by weight~55.2% by weight [53.8 wt. % (Sample 1), 51.8 wt. % (Sample 2), 50.2 wt. % (Sample 3), 55.2 wt. % (Sample 4) (average of Sample 1~Sample 4=52.8 wt. %)] of the total phosphatidylserine.

Incidentally, the fatty acids in the phosphatidylserine included: pentadecanoic acid 0.6±0.4 wt. %, palmitin acid 2.2±0.2 wt. %, margaric acid 1.0±0.2 wt. %, stearic acid 22.5±2.4 wt. %, palmitooleic acid 0.1±0.1 wt. %, oleic acid 1.0±0.2 wt. %, sis-vaccenic acid 0.5±0.1 wt. %, linoic acid 0.1±0.1 wt. %, α-linolenic acid 1.9±0.3 wt. %, arachidonic acid 1.5±0.7 wt. %, eicosapentaenoic acid 1.1±0.2 wt. %, docosatrienoic acid 1.7±0.3 wt. %, docosatetraenoic acid 5.6±0.4 wt. %, docosapentaenoic acid 4.8±0.4 wt. %, and docosahexaenoic acid 52.8±1.9 wt. %.

Therefore, according to the present embodiment, phosphatidylserine wherein the proportion of phosphatidylserine comprising docosahexaenoic acid is very high, i.e. 50% by weight or higher, was obtained.

The similar analyses were conducted to examine phosphatidylethanolamine. The phosphatidylethanolamine content was very high: 29.3% by weight~38.2% by weight [38.2 wt. % (Sample 1), 30.7 wt. % (Sample 2), 29.5 wt. % (Sample 3), 29.3 wt. % (Sample 4) (average of Sample 1~Sample 4=31.93 wt. %)] of the total amount of phospholipids. Also, the proportion of phosphatidylethanolamine comprising docosahexaenoic acid was very high: 46.0% by weight~50.9% by weight [49.2 wt. % (Sample 1), 50.9 wt. % (Sample 2), 46.0 wt. % (Sample 3), 50.9 wt. % (Sample 4) (average of Sample 1~Sample 4=49.3 wt. %)] of the total phosphatidylethanolamine.

Incidentally, the fatty acids in the phosphatidylethanolamine included: myristic acid 0.1±0.1 wt. %, pentadecanoic acid 0.3±0.1 wt. %, palmitin acid 19.8±1.1 wt. %, margaric acid 1.4±0.2 wt. %, stearic acid 8.4±0.6 wt. %, palmitooleic acid 0.6±0.2 wt. %, oleic acid 3.3±0.6 wt. %, sis-vaccenic acid 1.2±0.1 wt. %, linoic acid 0.3±0.1 wt. %, α-linolenic acid 0.2±0.1 wt. %, arachidonic acid 2.8±0.4 wt. %, eicosapentaenoic acid 2.1±0.4 wt. %, docosatrienoic acid 0.8±0.1 wt. %, docosatetraenoic acid 3.2±0.2 wt. %, docosapentaenoic acid 2.4±0.3 wt. %, and docosahexaenoic acid 49.3±2.0 wt. %.

Therefore, according to the present embodiment, phosphatidylethanolamine wherein the proportion of phosphatidylethanolamine comprising docosahexaenoic acid is very high, i.e. 45% by weight or higher, was obtained.

Embodiment 3

In the same manner as in the case of the testis of bonito in Embodiment 2, the testis of tuna was boiled, and a lipid mixture was obtained by extraction with ethanol followed by removal of the ethanol.

The lipid mixture obtained in this manner contained neutrolipids 34.2% by weight and phospholipids 65.8% by weight. Therefore, a lipid mixture with a high phospholipid content was obtained according to the present invention.

HPLC was employed to separate phosphatidylserine from the phospholipids in the lipid mixture obtained according to the present embodiment. The phosphatidylserine content was very high: 9.2% by weight~11.2% by weight [11.2 wt. % (Sample 1), 10.5 wt. % (Sample 2), 9.8 wt. % (Sample 3), 9.6 wt. % (Sample 4), 9.2 wt. % (Sample 5), (average of Sample 1~Sample 5=10.06 wt. %)] of the total amount of phospholipids. Also, analyses per GC were performed on the fatty acids in the phosphatidylserine. It was found that the proportion of phosphatidylserine comprising docosahexaenoic acid was very high: 46.9% by weight~53.2% by weight [50.1 wt. % (Sample 1), 46.9 wt. % (Sample 2), 53.2 wt. % (Sample 3), 51.0 wt. % (Sample 4), 50.5 wt. % (Sample 5), (average of Sample 1~Sample 5=50.3 wt. %)] of the total phosphatidylserine.

The similar analyses were conducted to examine phosphatidylethanolamine. The phosphatidylethanolamine content was very high: 26.8% by weight~31.1% by weight [31.1 wt. % (Sample 1), 29.9 wt. % (Sample 2), 27.8 wt. % (Sample 3), 26.9 wt. % (Sample 4), 26.8 wt. % (Sample 5) (average of Sample 1~Sample 5=28.50 wt. %)] of the total amount of phospholipids. Also, the proportion of phosphatidylethanolamine comprising docosahexaenoic acid was very high: 38.7% by weight~46.9% by weight [41.7 wt. % (Sample 1), 38.7 wt. % (Sample 2), 43.4 wt. % (Sample 3), 46.9 wt. % (Sample 4), 43.4 wt. % (Sample 5), (average of Sample 1~Sample 5=42.8 wt. %)] of the total phosphatidylethanolamine.

Therefore, according to the present embodiment, phosphatidylserine wherein the proportion of phosphatidylserine comprising docosahexaenoic acid is very high, i.e. 45% by weight or higher, was obtained. Also, phosphatidylethanolamine wherein the proportion of phosphatidylethanolamine comprising docosahexaenoic acid is very high, i.e. 35% by weight or higher, was obtained.

In the above embodiments 1, 2 and 3, the viscera of fish were processed in hot water at 60° C. or higher, and then extraction with a solvent was performed without changing the state of the viscera. However, this is not the only method according to the present invention. For example, the viscera of bonito or tuna may be dried after processing in hot water of 60° C. or higher, and after drying, extraction with a solvent may be performed.

According to the present invention, simply applying a convenient and low-cost hot water process before extraction can deactivate catabolic enzymes of phospholipids in the viscera of fish, making it possible to preserve the viscera for a long time. Furthermore, according to the present invention, a lipid mixture that has a high phospholipid content, a low impurity level, and very little fishy smell can be obtained. Furthermore, the present invention is nature- and health-oriented, because extraction is made from the viscera of natural fish. Furthermore, the present invention makes use of the viscera of fish, which are normally discarded, contributing to maximum resource utilization via a low-cost process. Furthermore, according to the present invention, a lipid mixture containing phosphatidylserine comprising docosahexaenoic acid and phosphatidylethanolamine comprising docosahexaenoic acid can be obtained. Specifically, the proportion of phosphatidylserine comprising docosahexaenoic acid is 45% by weight or higher of the total phosphatidylserine; and the proportion of phosphatidylethanolamine comprising docosahexaenoic acid is 35% by weight or higher of the total phosphatidylethanolamine.

Obviously, many modifications and variations of the present invention are possible in light of the above teachings. It is therefore to be understood that, within the scope of the appended claims, the invention may be practiced otherwise than as specifically described.

What is claimed is:

1. A method for extracting a lipid mixture, said method comprising the steps of:
   (a) heating viscera of fish using hot water or steam; and
   (b) extracting from the heated viscera of fish, using a solvent, the lipid mixture containing phospholipids comprising polyunsaturated fatty acids.

2. The method according to claim 1, further comprising the step of
(c) preserving the heated viscera of fish in refrigeration or frozen until the step of extracting the lipid mixture is applied.

3. The method according to claim 1, wherein the viscera are heated to a temperature of 60° C. or higher in the step (a).

4. The method according to claim 1, wherein the viscera are heated for 10 minutes to 180 minutes in the step (a).

5. The method according to claim 1, wherein the fish include bonito, tuna, mackerel, sardine, cod, sea bream, flounder, flatfish, shark, salmon, and trout.

6. The method according to claim 1, wherein the viscera include ovary, testis, heart, liver, stomach and intestines.

7. The method according to claim 1, wherein said lipid mixture contains phosphatidylserine comprising docosahexaenoic acid and phosphatidylethanolamine comprising docosahexaenoic acid.

8. The method according to claim 1, further comprising the step of
(d) extracting phosphatidylserine or phosphatidylethanolamine by separating said lipid mixture.

9. The method according to claim 1, wherein said lipid mixture is extracted by use of either an organic solvent or a mixed solvent of an organic solvent and water in the step (b).

10. A method for preserving viscera of fish for a predetermined time period before extracting, using a solvent, a lipid mixture containing phospholipids comprising polyunsaturated fatty acids, said method comprising the steps of:

(a) heating the viscera of fish; and (b) preserving the heated viscera in refrigeration or by freezing.

* * * * *